US010194787B2

(12) United States Patent
Li et al.

(10) Patent No.: US 10,194,787 B2
(45) Date of Patent: Feb. 5, 2019

(54) ENDOSCOPE AND METHOD OF MANUFACTURING THE SAME, AND MEDICAL DETECTION SYSTEM

(71) Applicant: BOE TECHNOLOGY GROUP CO., LTD., Beijing (CN)

(72) Inventors: Zhenglong Li, Beijing (CN); Lijie Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 223 days.

(21) Appl. No.: 15/159,132

(22) Filed: May 19, 2016

(65) Prior Publication Data
US 2017/0065158 A1    Mar. 9, 2017

(30) Foreign Application Priority Data

Sep. 9, 2015    (CN) .......................... 2015 1 0571554

(51) Int. Cl.
A61B 1/06          (2006.01)
A61B 1/04          (2006.01)
(Continued)

(52) U.S. Cl.
CPC .......... A61B 1/041 (2013.01); A61B 1/00004 (2013.01); A61B 1/0011 (2013.01);
(Continued)

(58) Field of Classification Search
CPC ................ A61B 1/0011; A61B 1/041; A61M 2025/1031; A61L 2420/02; A61L 2420/08; C03B 2215/31
(Continued)

(56) References Cited

U.S. PATENT DOCUMENTS 3,596,095 A  *  7/1971  Leach ................... C09K 11/08
                                                        250/461.1
6,984,205 B2 *  1/2006  Gazdzinski ........ A61B 1/00016
                                                        600/160
(Continued)

FOREIGN PATENT DOCUMENTS

CN    101351146 A    1/2009
CN    101437568 A    5/2009
(Continued)

OTHER PUBLICATIONS

1st office action issued in corresponding Chinese application No. 201510571554.1 dated Apr. 5, 2016.

*Primary Examiner* — Timothy J Neal
*Assistant Examiner* — Jae Woo
(74) *Attorney, Agent, or Firm* — Nath, Goldberg & Meyer; Joshua B. Goldberg

(57) ABSTRACT

The present invention discloses an endoscope and a method of manufacturing the endoscope, and a medical detection system. The endoscope includes a housing; and a transparent cover structure, which includes a seal cover and at least one dissolution layer, the at least one dissolution layer wrapping around an outer surface of the seal cover, and the dissolution layer including a soluble material that can dissolve in digestive juices, wherein the housing and the transparent cover structure are connected in a sealed manner to form a sealed space, and the sealed space is provided therein with: an optical lens, which is provided in a region of the sealed space close to the transparent cover structure; a light source, which is provided in a region around the optical lens; and an image sensor, which is provided to correspond with the optical lens.

12 Claims, 2 Drawing Sheets

(51) Int. Cl.
*A61B 1/273* (2006.01)
*A61B 1/00* (2006.01)

(52) U.S. Cl.
CPC ...... *A61B 1/00016* (2013.01); *A61B 1/00032* (2013.01); *A61B 1/00071* (2013.01); *A61B 1/06* (2013.01); *A61B 1/2736* (2013.01)

(58) Field of Classification Search
USPC .......................................... 600/160, 103, 117
See application file for complete search history.

(56) References Cited

U.S. PATENT DOCUMENTS

| | | | | |
|---|---|---|---|---|
| 7,993,263 | B2* | 8/2011 | Yokoi | A61B 1/00016 600/109 |
| 8,852,083 | B2* | 10/2014 | Mintchev | A61B 1/041 600/116 |
| 9,795,330 | B2* | 10/2017 | Pascal | A61B 5/1459 |
| 2003/0216622 | A1* | 11/2003 | Meron | A61B 1/00147 600/300 |
| 2004/0181155 | A1* | 9/2004 | Glukhovsky | A61B 1/00147 600/476 |
| 2005/0137468 | A1* | 6/2005 | Avron | A61B 1/041 600/310 |
| 2006/0034514 | A1* | 2/2006 | Horn | A61B 1/00009 382/181 |
| 2006/0155174 | A1* | 7/2006 | Glukhovsky | A61B 1/00036 600/301 |
| 2006/0178557 | A1 | 8/2006 | Mintchev et al. | |
| 2007/0177075 | A1* | 8/2007 | Kimoto | A61B 1/00048 349/110 |
| 2007/0225552 | A1* | 9/2007 | Segawa | A61B 1/041 600/102 |
| 2007/0249900 | A1* | 10/2007 | Wilson | A61B 1/00036 600/116 |
| 2007/0255098 | A1* | 11/2007 | Wang | A61B 1/041 600/109 |
| 2008/0114225 | A1* | 5/2008 | Rabinovitz | A61B 1/041 600/310 |
| 2008/0255409 | A1* | 10/2008 | Graumann | A61B 1/041 600/101 |
| 2008/0294005 | A1* | 11/2008 | Honda | A61B 1/00016 600/118 |
| 2009/0287121 | A1* | 11/2009 | Kawano | A61B 1/041 600/593 |
| 2009/0299231 | A1* | 12/2009 | Takizawa | A61B 1/041 600/593 |
| 2010/0324381 | A1* | 12/2010 | Glukhovsky | A61B 1/00036 600/302 |
| 2011/0092787 | A1* | 4/2011 | Bulitta | A61B 1/00016 600/364 |
| 2016/0095499 | A1* | 4/2016 | Trollsas | A61B 5/073 600/109 |
| 2016/0287058 | A1* | 10/2016 | Ye | A61B 1/00158 |
| 2016/0353978 | A1* | 12/2016 | Miller | A61B 1/00096 |
| 2017/0100086 | A1* | 4/2017 | Takasugi | A61B 6/481 |
| 2017/0245742 | A1* | 8/2017 | Hadley | A61B 1/041 |

FOREIGN PATENT DOCUMENTS

| | | |
|---|---|---|
| CN | 201855253 U | 6/2011 |
| CN | 102631183 A | 8/2012 |
| CN | 202459518 U | 10/2012 |
| CN | 102920418 A | 2/2013 |
| WO | 2004/054430 A2 | 7/2004 |

\* cited by examiner

ENDOSCOPE AND METHOD OF MANUFACTURING THE SAME, AND MEDICAL DETECTION SYSTEM

FIELD OF THE INVENTION

The present invention relates to the field of medical detection technology, and in particular relates to an endoscope and a method of manufacturing the same, and a medical detection system.

BACKGROUND OF THE INVENTION

An existing capsule endoscope is an endoscope shaped like a capsule. The capsule endoscope can enter a human body to examine the health status of the digestive system of the human body, thus helping doctors diagnose patients.

The existing capsule endoscope typically includes a transparent cover, a light source, an optical imaging device, a battery, an antenna and the like. The transparent cover can protect the optical imaging device. In practice, in order to reduce such phenomena that sticky objects inside the digestive system adhere to the transparent cover and thus affect the imaging, a patient is usually required to strictly follow a diet, that is, to have liquid food in the daytime of the day before examination with the capsule endoscope, to fast from the evening of that day to the day of the examination, and to have a small amount of food only after four hours from the time when the capsule endoscope leaves the human body. Such diet of fasting or eating less brings great inconvenience to patients, especially to those of weak constitution. Moreover, considering the complexity of the digestive system of a human body, even if the diet is strictly followed, it is still impossible to completely eradicate the phenomena that sticky objects inside the digestive system adhere to the transparent cover and thus affect the imaging.

SUMMARY OF THE INVENTION

In order to address the above problem, the present invention provides an endoscope and a method of manufacturing the endoscope, and a medical detection system, which are used for dealing with the problem of the existing capsule endoscope that sticky objects adhere to the transparent cover and thus affect the imaging.

To this end, the present invention provides an endoscope, comprising a housing and a transparent cover structure, the transparent cover structure including a seal cover and at least one dissolution layer, the at least one dissolution layer wrapping around an outer surface of the seal cover, and the dissolution layer including a soluble material that can dissolve in digestive juices. The housing and the transparent cover structure are connected in a sealed manner to form a sealed space, and the sealed space is provided therein with: an optical lens, which is provided in a region of the sealed space close to the transparent cover structure; a light source, which is provided in a region around the optical lens; and an image sensor, which is provided to correspond with the optical lens.

Optionally, the at least one dissolution layer includes a plurality of dissolution layers and at least one bonding layer, and the bonding layer is provided between adjacent dissolution layers of the plurality of dissolution layers.

Optionally, the bonding layer includes a transparent water-soluble material.

Optionally, the optical lens includes a fisheye lens.

Optionally, the seal cover includes a corrosion-resistant polymer material.

Optionally, the digestive juices include a digestive juice from at least one of small intestine, large intestine, and stomach.

Optionally, the endoscope further comprises: a power source, which is provided in a center region of the sealed space; an antenna, which is provided in a region of the sealed space far from the transparent cover structure; and a processor, which is provided between the power source and the antenna, wherein the light source, the image sensor and the processor are each connected to the power source.

The present invention also provides a medical detection system, comprising an information receiving device and the above endoscope. The information receiving device is used for receiving image information collected by the endoscope.

The present invention also provides a method of manufacturing an endoscope, comprising: forming a housing; forming a transparent cover structure, which includes a seal cover and at least one dissolution layer, the at least one dissolution layer wrapping around an outer surface of the seal cover, and the dissolution layer including a soluble material that can dissolve in digestive juices; connecting the housing and the transparent cover structure in a sealed manner to form a sealed space; and providing in the sealed space: an optical lens, which is provided in a region of the sealed space close to the transparent cover structure; a light source, which is provided in a region around the optical lens; and an image sensor, which is provided to correspond with the optical lens.

Optionally, the at least one dissolution layer includes a plurality of dissolution layers and at least one bonding layer, and the bonding layer is provided between adjacent dissolution layers of the plurality of dissolution layers.

Optionally, the bonding layer includes a transparent water-soluble material.

Optionally, the optical lens includes a fisheye lens.

Optionally, the seal cover includes a corrosion-resistant polymer material.

Optionally, the method of manufacturing an endoscope further comprises: providing in the sealed space: a power source, which is provided in a center region of the sealed space; an antenna, which is provided in a region of the sealed space far from the transparent cover structure; and a processor, which is provided between the power source and the antenna, wherein the light source, the image sensor and the processor are each connected to the power source.

The present invention has the following beneficial effect:

The endoscope and the method of manufacturing the endoscope, and the medical detection system provided by the present invention can realize the following effect: when a sticky object inside the digestive system adheres to the outer surface of the transparent cover structure, as the dissolution layer contacting the sticky object gradually dissolves, the sticky object also gradually falls off the transparent cover structure, so that the sticky object once adhering to the outer surface of the transparent cover structure no longer affects the imaging process of the optical imaging device, thereby improving the imaging quality of the endoscope.

DETAILED DESCRIPTION OF THE EMBODIMENTS

In order to provide a better understanding of the technical solutions of the present invention to the skilled in the art, an endoscope and a method of manufacturing the endoscope, and a medical detection system provided in the invention are described below in detail in conjunction with the drawings.

Embodiment 1

Figure 1:
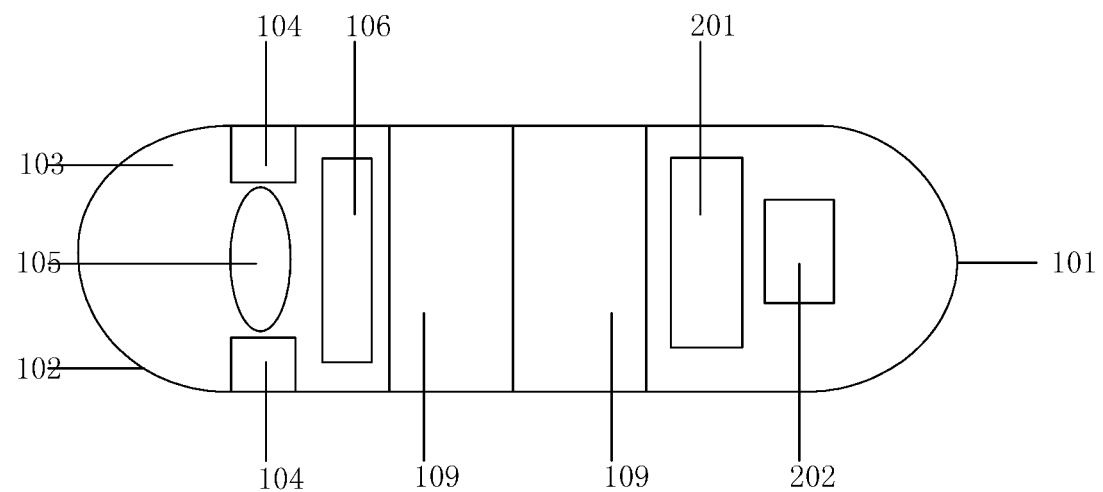
FIG. 1 is a schematic diagram of a structure of an endoscope provided in Embodiment 1 of the present invention.
Figure 2:
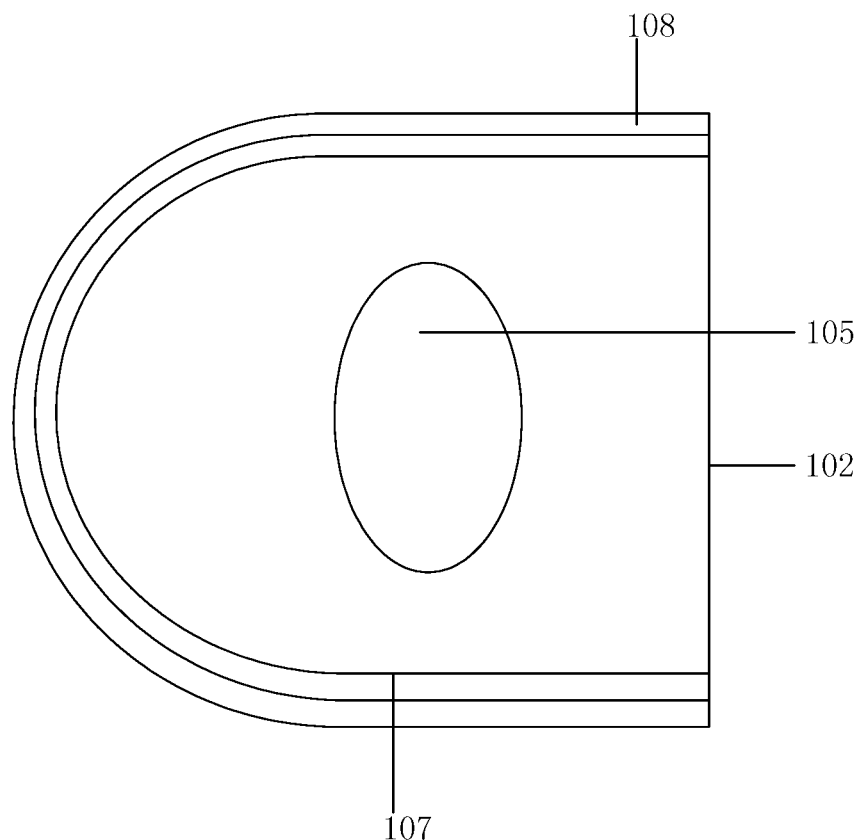
FIG. 2 is a schematic diagram of a structure of a transparent cover structure provided in Embodiment 1 of the present invention.

FIG. 1 is a schematic diagram of a structure of an endoscope provided in Embodiment 1 of the present invention; FIG. 2 is a schematic diagram of a structure of a transparent cover structure provided in Embodiment 1 of the present invention. As shown in FIG. 1 and FIG. 2, the endoscope includes a housing 101 and a transparent cover structure 102, the housing 101 and the transparent cover structure 102 are connected in a sealed manner to form a sealed space 103, and a light source 104, an optical lens 105 and an image sensor 106 are provided in the sealed space 103. The optical lens is provided in a region of the sealed space 103 close to the transparent cover structure 102, the light source 104 is provided in a region around the optical lens, and the image sensor 106 is provided to correspond with the optical lens 105.

The structure of the endoscope may be generally divided, according to the function, into two portions: an imaging portion and a signal transmission portion. The left half part of FIG. 1 shows the structure of the imaging portion. The transparent cover structure 102 has two functions: protecting a set of imaging elements (the light source 104, the optical lens 105 and the image sensor 106) inside the transparent cover; and preventing sticky objects in the digestive system from adhering to the transparent cover and affecting the imaging. The light source 104 provides illumination for imaging in the digestive system. The optical lens 105 projects the incoming light transmitting through the transparent cover onto the image sensor 106, to realize a process of photoelectric conversion imaging.

The right half part of FIG. 1 shows the signal transmission portion. The signal processor 201 receives image signals transmitted from the set of imaging elements, compresses the image signals, and transmits them to an external receiving device through the antenna 202. The middle part of the endoscope shows a power source, which is usually a battery pack.

Figure 3:
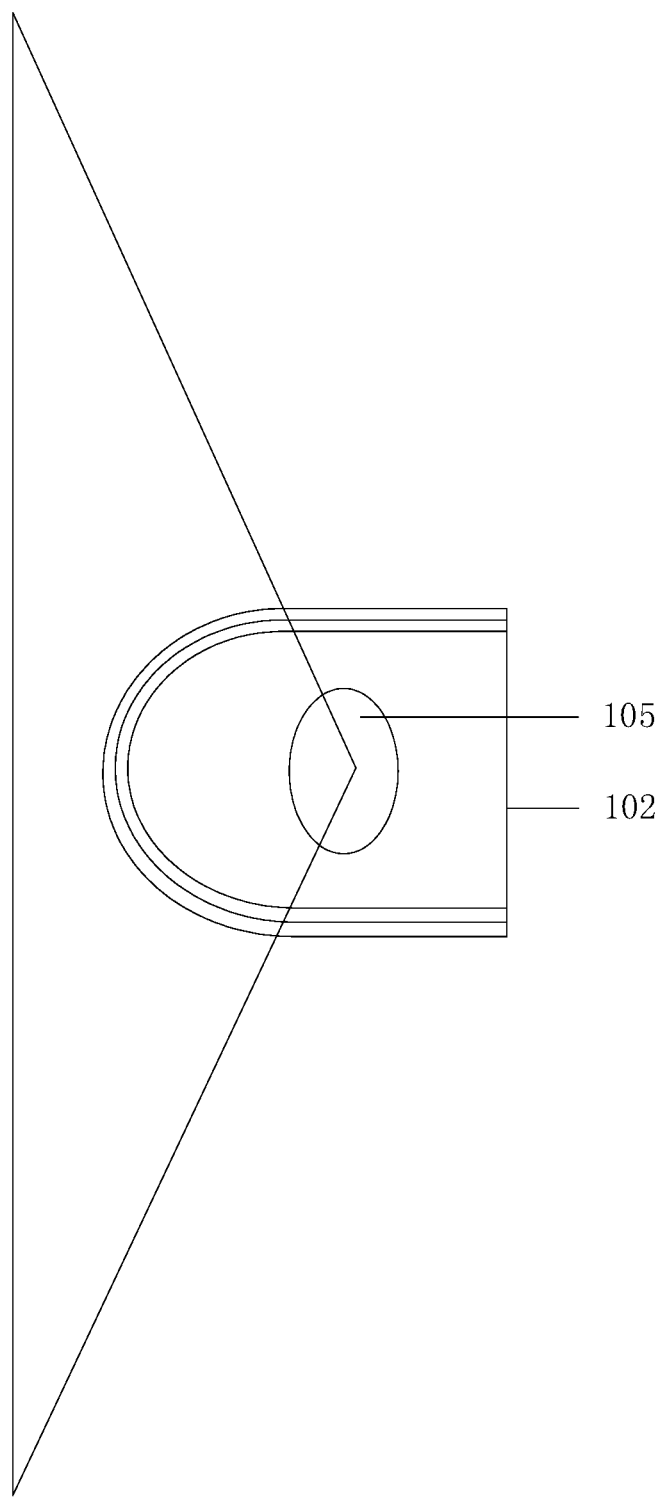
FIG. 3 is a functional schematic diagram of a fisheye lens provided in Embodiment 1 of the present invention.

In order to obtain a larger angle of view, usually the size of the optical lens needs to be increased, or the focal length of the optical lens needs to be adjusted. However, due to the limitation of the total dimension of the endoscope, the size of the optical lens cannot be significantly increased, and the optical lens in the endoscope can only be a lens with a fixed focal length, i.e. its focal length is not adjustable. Hence, the above method for obtaining a larger angle of view by increasing the size of the optical lens or by adjusting the focal length of the optical lens is hardly feasible with a limited dimension of the endoscope. To address the above problem, the present embodiment utilizes a fisheye lens to obtain a larger angle of view. Referring to FIG. 3, FIG. 3 is a functional schematic diagram of a fisheye lens provided in Embodiment 1 of the present invention. As shown in FIG. 3, the optical lens includes a fisheye lens 105. The fisheye lens provided in the present embodiment can obtain an angle of view approaching 180 degrees, without increasing the size of the lens in the optical lens. Thus, compared to an ordinary optical lens, the fisheye lens provided in the present embodiment, which is an ultra wide angle lens with an angle of view approaching 180 degrees, can obtain a larger angle of view, and is thus able to collect more image information.

Referring to FIG. 2, the transparent cover structure 102 includes a seal cover 107 and at least one dissolution layer 108, the at least one dissolution layer 108 wraps around an outer surface of the seal cover 107, and the dissolution layer 108 includes a soluble material that can dissolve in digestive juices. In practical applications, when a sticky object inside the digestive system adheres to the outer surface of the transparent cover structure, as the dissolution layer contacting the sticky object gradually dissolves, the sticky object also gradually falls off the transparent cover structure, so that the sticky object once adhering to the outer surface of the transparent cover structure no longer affects the imaging process of the optical imaging device (that is, the optical lens 105 and the image sensor 106), thereby improving the imaging quality of the endoscope.

Material of the dissolution layer in the present embodiment can be selected or prepared based on the application of the endoscope. For example, the dissolution layer of the transparent cover of an endoscope used for stomach examination may include a substance apt to react with gastric acid, such as gelatin that has gone through special physicochemical treatment. As another example, the dissolution layer of the transparent cover of an endoscope used for intestinal examination may include a substance that is not apt to react with gastric acid, and a substance soluble in intestinal digestive juices, for example, for an enteric coated capsule with a gelatin housing, a polymer membrane can be coated on the gelatin housing, and such membrane is stable in an acid environment, but would be disintegrated quickly in a weak acid or alkaline environment. Of course, other aspects may also be considered when selecting material of the dissolution layer, as long as it is ensured that the dissolution layer is soluble in any one of digestive juices.

Optionally, as shown in FIG. 2, the dissolution layer may have a composite multi-layer structure. A bonding layer is provided between two adjacent dissolution layers to bond the two together. Time needed for dissolution of the dissolution layer can be controlled by controlling the number of layers of the multi-layer structure. The bonding layer may be made of a material that bonds the layers to each other and is extremely apt to dissolve in digestive juices, for example, a transparent water-soluble material. The advantage of providing the bonding layer is that: it dissolves with the dissolution of a dissolution layer, and it causes the remaining dissolution layers to fall off along with it, which better prevents sticky objects adhering to the outer surface of the transparent cover structure from affecting the imaging. Optionally, the seal cover 107 includes a corrosion-resistant polymer material, and the digestive juices include a digestive juice from at least one of small intestine, large intestine, and stomach. In other words, the endoscope provided in the present embodiment can be applied to examinations of various digestive organs in the digestive system such as stomach, small intestine or large intestine.

Referring to FIG. 1, the endoscope also includes a power source 109, a processor 201 and an antenna 202, the power source 109 is provided in a center region of the sealed space 103, the antenna 202 is provided in a region of the sealed space 103 far from the transparent cover structure 102, the processor 201 is provided between the power source 109 and the antenna 202, and the light source 104, the image sensor 106 and the processor 201 are each connected to the power source 109.

The endoscope provided in the present embodiment is a wireless capsule endoscope (WCE), which is a special endoscope shaped like a capsule. After a patient swallows the capsule, the endoscope collects image information inside the digestive system through the self-carrying optical imaging device (i.e. the optical lens 105 and the image sensor 106), and transmits the image information inside the digestive system to an in-vitro image receiving device through the self-carrying wireless transmission device (i.e. the antenna 202), and the image receiving device synthesizes the received image information into an image for doctors' diagnostic use.

The endoscope provided in the present embodiment can achieve the following effect: when a sticky object inside the digestive system adheres to the outer surface of the transparent cover structure, as the dissolution layer contacting the sticky object gradually dissolves, the sticky object also gradually falls off the transparent cover structure, so that the sticky object once adhering the outer surface of the transparent cover structure no longer affects the imaging process of the optical imaging device, thereby improving the imaging quality of the endoscope.

Embodiment 2

The present embodiment provides a medical detection system, comprising an information receiving device and the endoscope provided in the above Embodiment 1, and the information receiving device is used for receiving image information collected by the endoscope. As for the detailed structure of the endoscope, one can refer to the description in the above Embodiment 1, which is not repeated herein.

In the present embodiment, the endoscope collects image information inside the digestive system through the self-carrying optical imaging device (i.e. the optical lens 105 and the image sensor 106), and transmits the image information inside the digestive system to an in-vitro image receiving device through the wireless transmission device (i.e. the antenna 202), and the image receiving device receives the image information collected by the endoscope, and synthesizes the received image information into an image for doctors' diagnostic use.

The medical detection system provided in the present embodiment can achieve the following effect: when a sticky object inside the digestive system adheres to the outer surface of the transparent cover structure, as the dissolution layer contacting the sticky object gradually dissolves, the sticky object also gradually falls off the transparent cover structure, so that the sticky object once adhering to the outer surface of the transparent cover structure no longer affects the imaging process of the optical imaging device, thereby improving the imaging quality of the endoscope.

Embodiment 3

The present embodiment provides a method of manufacturing an endoscope, comprising: forming a housing; forming a transparent cover structure, which includes a seal cover and at least one dissolution layer, the at least one dissolution layer wrapping around an outer surface of the seal cover, and the dissolution layer including a soluble material that can dissolve in digestive juices; connecting the housing and the transparent cover structure in a sealed manner to form a sealed space; and providing the following components in the sealed space: an optical lens, which is provided in a region of the sealed space close to the transparent cover structure; a light source, which is provided in a region around the optical lens; and an image sensor, which is provided to correspond with the optical lens.

Material of the dissolution layer in the present embodiment can be selected or prepared based on the application of the endoscope. For example, the dissolution layer of the transparent cover of an endoscope used for stomach examination may include a substance apt to react with gastric acid, such as gelatin that has gone through special physicochemical treatment. As another example, the dissolution layer of the transparent cover of an endoscope used for intestinal examination may include a substance that is not apt to react with gastric acid, and a substance soluble in intestinal digestive juices, for example, for an enteric coated capsule with a gelatin housing, a polymer membrane can be coated on the gelatin housing, and such membrane is stable in an acid environment, but would be disintegrated quickly in a weak acid or alkaline environment. Of course, other aspects may also be considered when selecting materials of the dissolution layer, as long as it is ensured that the dissolution layer is soluble in any one of digestive juices.

Optionally, as shown in FIG. 2, the dissolution layer may have a composite multi-layer structure. A bonding layer is provided between two adjacent dissolution layers to bond the two together. The bonding layer may be made of a material that bonds the layers to each other and is extremely apt to dissolve in digestive juices, for example, a transparent water-soluble material. The advantage of providing the bonding layer is that: it dissolves with the dissolution of a dissolution layer, and it causes the remaining dissolution layers to fall off along with it, which better prevents sticky objects adhering to the outer surface of the transparent cover structure from affecting the imaging.

If the dissolution layer is a multi-layer structure, time needed for dissolution of the dissolution layer can be controlled by controlling the number of layers of the multi-layer structure. Specifically, when the endoscope is used for stomach examination, an appropriate number of the dissolution layers may be determined based on the gastric emptying time, the property of gastric juice (such as pH value), the resistance time of the endoscope inside the stomach, the time (which may be determined by experiments, for example) needed for dissolution of a single dissolution layer made of a material suitable for stomach examination and the like, so that sticky objects that adhere to the outer surface of the transparent cover structure fall off in time during the examination with the endoscope.

In order to obtain a larger angle of view, usually the size of the optical lens needs to be increased, or the focal length of the optical lens needs to be adjusted. However, due to the limitation of the total dimension of the endoscope, the size of the optical lens cannot be significantly increased, and the optical lens in the endoscope can only be a lens with a fixed focal length, i.e. its focal length is not adjustable. Hence, the above method for obtaining a larger angle of view by increasing the size of the optical lens or by adjusting the focal length is hardly feasible with a limited dimension of the endoscope. To address the above problem, optionally, the optical lens may include a fisheye lens. Referring to FIG. 3, the fisheye lens provided in the present embodiment can obtain an angle of view approaching 180 degrees, without increasing the size of the lens in the optical lens. Thus, compared to an ordinary optical lens, the fisheye lens provided in the present embodiment, which is an ultra wide angle lens with an angle of view approaching 180 degrees, can obtain a larger angle of view, and is thus able to collect more image information.

Optionally, the seal cover includes a corrosion-resistant polymer material, and the digestive juices include a digestive juice from at least one of small intestine, large intestine, and stomach. In other words, the endoscope manufactured using the method provided in the present embodiment can be applied to examinations of various digestive organs in the digestive system such as stomach, small intestine or large intestine.

Referring to FIG. 1, the endoscope also includes a power source 109, a processor 201 and an antenna 202, the power source 109 is provided in a center region of the sealed space 103, the antenna 202 is provided in a region of the sealed space 103 far from the transparent cover structure 102, the processor 201 is provided between the power source 109 and the antenna 202, and the light source 104, the image sensor 106 and the processor 201 are each connected to the power source 109.

The endoscope manufactured using the method provided in the present embodiment can achieve the following effect: when a sticky object inside the digestive system adheres to the outer surface of the transparent cover structure, as the dissolution layer contacting the sticky object gradually dissolves, the sticky object also gradually falls off the transparent cover structure, so that the sticky object once adhering the outer surface of the transparent cover structure no longer affects the imaging process of the optical imaging device, thereby improving the imaging quality of the endoscope.

It can be understood that the foregoing implementations are merely exemplary implementations used for describing the principle of the present invention, but the present invention is not limited thereto. Those of ordinary skill in the art may make various variations and modifications without departing from the spirit and essence of the present invention, and these variations and modifications shall fall into the protection scope of the present invention.

The invention claimed is:

1. An endoscope, comprising:
a housing; and
a transparent cover structure, which includes a seal cover and at least one dissolution layer, the at least one dissolution layer wrapping around an outer surface of the seal cover, and the at least one dissolution layer including a material that is soluble in digestive juices,
wherein the housing and the transparent cover structure are connected in a sealed manner to form a sealed space, and the sealed space is provided therein with:
an optical lens, which is provided in a region of the sealed space close to the transparent cover structure;
a light source, which is provided in a region around the optical lens; and
an image sensor, which is provided to correspond with the optical lens,
wherein the at least one dissolution layer includes a plurality of dissolution layers and at least one bonding layer, and the bonding layer is provided between adjacent dissolution layers of the plurality of dissolution layers.

2. The endoscope according to claim 1, wherein the bonding layer includes a transparent water-soluble material.

3. The endoscope according to claim 1, wherein the optical lens includes a fisheye lens.

4. The endoscope according to claim 1, wherein the seal cover includes a corrosion-resistant polymer material.

5. The endoscope according to claim 1, wherein the dissolution layer comprises a dissolvable material that is soluble in digestive juice from at least one of small intestine, large intestine, and stomach.

6. The endoscope according to claim 1, further comprising:
a power source, which is provided in a center region of the sealed space;
an antenna, which is provided in a region of the sealed space far from the transparent cover structure; and
a processor, which is provided between the power source and the antenna,
wherein the light source, the image sensor and the processor are each connected to the power source.

7. A medical detection system, comprising:
the endoscope according to claim 1; and
an information receiving device, which is used for receiving image information collected by the endoscope.

8. A method of manufacturing an endoscope, comprising:
forming a housing;
forming a transparent cover structure, which includes a seal cover and at least one dissolution layer, the at least one dissolution layer wrapping around an outer surface of the seal cover, and the at least one dissolution layer including a material that is soluble in digestive juices;
connecting the housing and the transparent cover structure in a sealed manner to form a sealed space; and
in the sealed space, providing:
an optical lens, which is provided in a region of the sealed space close to the transparent cover structure;
a light source, which is provided in a region around the optical lens; and
an image sensor, which is provided to correspond with the optical lens,
wherein the at least one dissolution layer includes a plurality of dissolution layers and at least one bonding layer, and the bonding layer is provided between adjacent dissolution layers of the plurality of dissolution layers.

9. The method of manufacturing an endoscope according to claim 8, wherein the bonding layer includes a transparent water-soluble material.

10. The method of manufacturing an endoscope according to claim 8, wherein the optical lens includes a fisheye lens.

11. The method of manufacturing an endoscope according to claim 8, wherein the seal cover includes a corrosion-resistant polymer material.

12. The method of manufacturing an endoscope according to claim 8, further comprising:
in the sealed space, providing:
a power source, which is provided in a center region of the sealed space;
an antenna, which is provided in a region of the sealed space far from the transparent cover structure; and
a processor, which is provided between the power source and the antenna,
wherein the light source, the image sensor and the processor are each connected to the power source.

* * * * *